United States Patent
Kameoka et al.

(10) Patent No.: US 7,105,810 B2
(45) Date of Patent: *Sep. 12, 2006

(54) ELECTROSPRAY EMITTER FOR MICROFLUIDIC CHANNEL

(75) Inventors: Jun Kameoka, Ithaca, NY (US); Harold G. Craighead, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 48 days.

This patent is subject to a terminal disclaimer.

(21) Appl. No.: 10/394,757

(22) Filed: Mar. 21, 2003

(65) Prior Publication Data
US 2003/0213918 A1 Nov. 20, 2003

Related U.S. Application Data
(60) Provisional application No. 60/342,625, filed on Dec. 21, 2001, and provisional application No. 60/366,448, filed on Mar. 12, 2002.

(51) Int. Cl.
*H01J 49/00* (2006.01)
*B01D 54/44* (2006.01)

(52) U.S. Cl. .................. 250/288; 210/656; 210/748
(58) Field of Classification Search ............ 250/288, 250/281, 282; 210/656, 748, 198.2
See application file for complete search history.

(56) References Cited

U.S. PATENT DOCUMENTS

| | | | | |
|---|---|---|---|---|
| 4,443,319 A | * | 4/1984 | Chait et al. | |
| 4,483,885 A | * | 11/1984 | Chait et al. | |
| 4,963,736 A | * | 10/1990 | Douglas et al. | |
| 5,296,114 A | * | 3/1994 | Manz | |
| RE34,757 E | | 10/1994 | Smith et al. | |
| 5,358,618 A | * | 10/1994 | Ewing et al. | |
| 5,395,975 A | * | 2/1995 | Hail et al. | |
| 5,423,964 A | | 6/1995 | Smith et al. | |
| 5,599,432 A | | 2/1997 | Manz et al. | |
| 5,624,539 A | | 4/1997 | Ewing et al. | |
| 5,705,813 A | * | 1/1998 | Apffel et al. | 250/288 |
| 5,716,825 A | * | 2/1998 | Hancock et al. | 435/286.5 |

(Continued)

FOREIGN PATENT DOCUMENTS

| | | |
|---|---|---|
| EP | 0653631 B1 | 5/1995 |
| GB | 2379554 A | 3/2003 |
| WO | WO-9111015 A1 | 7/1991 |

(Continued)

OTHER PUBLICATIONS

Bings, Nicolas H., et al., "Microfluidic Devices Connected to Fused–Silica Capillaries with Minimal Dead Volume", *Anal. Chem., 71*, (1999),3292–3296

(Continued)

*Primary Examiner*—John R. Lee
*Assistant Examiner*—Kalimah Fernandez
(74) *Attorney, Agent, or Firm*—Schwegman, Lundberg, Woessner & Kluth, P.A.

(57) ABSTRACT

An electrospray ionization device incorporates a shaped thin film with a microfluidic channel. The device may be interfaced to a time-of-flight mass spectrometer (TFOMS). In one embodiment, the shaped thin film has a polygonal-shaped or triangle-shaped thin polymer tip formed by lithography and etching. The microfluidic channel is approximately 20 micrometer wide and 10 micrometers deep, and embossed in a substrate using a silicon master. The shaped thin film is aligned with the channel and bonded between the channel substrate and a flat plate to create a microfluidic channel with a wicking tip protruding from the end of the channel. Application of a high voltage at one end of the channel creates an electrospray from the tip, which is provided to the TFOMS.

58 Claims, 5 Drawing Sheets

U.S. PATENT DOCUMENTS

| | | | |
|---|---|---|---|
| 5,800,690 A | | 9/1998 | Chow et al. |
| 5,833,861 A | | 11/1998 | Afeyan et al. |
| 5,856,671 A | | 1/1999 | Henion et al. |
| 5,858,188 A | | 1/1999 | Soane et al. |
| 5,858,195 A | | 1/1999 | Ramsey |
| 5,866,345 A | * | 2/1999 | Wilding et al. ............ 435/7.21 |
| 5,872,010 A | * | 2/1999 | Karger et al. ................ 436/173 |
| 5,885,470 A | | 3/1999 | Parce et al. |
| 5,917,184 A | | 6/1999 | Carson et al. |
| 5,935,401 A | | 8/1999 | Amigo |
| 5,958,202 A | | 9/1999 | Regnier et al. |
| 5,965,001 A | | 10/1999 | Chow et al. |
| 5,969,353 A | * | 10/1999 | Hsieh ......................... 250/288 |
| 5,993,633 A | | 11/1999 | Smith et al. |
| 5,994,696 A | * | 11/1999 | Tai et al. .................... 250/288 |
| 6,001,229 A | | 12/1999 | Ramsey |
| 6,010,607 A | | 1/2000 | Ramsey |
| 6,010,608 A | | 1/2000 | Ramsey |
| 6,012,902 A | | 1/2000 | Parce |
| 6,033,546 A | | 3/2000 | Ramsey |
| 6,033,628 A | * | 3/2000 | Kaltenbach et al. ....... 422/68.1 |
| 6,054,034 A | | 4/2000 | Soane et al. |
| 6,056,860 A | | 5/2000 | Amigo et al. |
| 6,068,749 A | | 5/2000 | Karger et al. |
| 6,086,243 A | | 7/2000 | Paul et al. |
| 6,110,343 A | | 8/2000 | Ramsey et al. |
| 6,123,798 A | | 9/2000 | Gandhi et al. |
| 6,139,734 A | | 10/2000 | Settlage et al. |
| 6,149,870 A | | 11/2000 | Parce et al. |
| 6,156,181 A | | 12/2000 | Parce et al. |
| 6,159,739 A | | 12/2000 | Weigl et al. |
| 6,176,962 B1 | | 1/2001 | Soane et al. |
| 6,187,190 B1 | | 2/2001 | Smith et al. |
| 6,231,737 B1 | | 5/2001 | Ramsey et al. |
| 6,238,538 B1 | | 5/2001 | Parce et al. |
| 6,240,790 B1 | | 6/2001 | Swedberg et al. |
| 6,245,227 B1 | | 6/2001 | Moon et al. |
| 6,277,641 B1 | | 8/2001 | Yager |
| 6,280,589 B1 | | 8/2001 | Manz et al. |
| 6,284,113 B1 | * | 9/2001 | Bjornson et al. ............ 204/453 |
| 6,284,115 B1 | | 9/2001 | Apffel |
| 6,297,499 B1 | | 10/2001 | Fenn |
| 6,318,970 B1 | | 11/2001 | Backhouse |
| 6,322,682 B1 | | 11/2001 | Arvidsson et al. |
| 6,326,616 B1 | | 12/2001 | Andrien, Jr. et al. |
| 6,337,740 B1 | | 1/2002 | Parce |
| 6,342,142 B1 | | 1/2002 | Ramsey |
| 6,368,562 B1 | | 4/2002 | Yao |
| 6,375,817 B1 | | 4/2002 | Taylor et al. |
| 6,394,942 B1 | | 5/2002 | Moon et al. |
| 6,409,900 B1 | | 6/2002 | Parce et al. |
| 6,413,401 B1 | | 7/2002 | Chow et al. |
| 6,416,642 B1 | * | 7/2002 | Alajoki et al. .............. 204/451 |
| 6,417,510 B1 | | 7/2002 | Moon et al. |
| 6,423,198 B1 | | 7/2002 | Manz et al. |
| 6,432,311 B1 | | 8/2002 | Moon et al. |
| 6,444,461 B1 | | 9/2002 | Knapp et al. |
| 6,450,047 B1 | | 9/2002 | Swedberg et al. |
| 6,450,189 B1 | * | 9/2002 | Ganan-Calvo ............... 137/12 |
| 6,454,924 B1 | | 9/2002 | Jedrzejewski et al. |
| 6,454,938 B1 | | 9/2002 | Moon et al. |
| 6,459,080 B1 | * | 10/2002 | Yin et al. .................... 250/288 |
| 6,461,516 B1 | | 10/2002 | Moon et al. |
| 6,462,337 B1 | | 10/2002 | Li et al. |
| 6,464,866 B1 | | 10/2002 | Moon et al. |
| 6,465,776 B1 | | 10/2002 | Moini et al. |
| 6,475,363 B1 | | 11/2002 | Ramsey |
| 6,475,441 B1 | | 11/2002 | Parce et al. |
| 6,481,648 B1 | | 11/2002 | Zimmermann |
| 6,491,804 B1 | | 12/2002 | Manz et al. |
| 6,495,016 B1 | | 12/2002 | Nawracala |
| 6,500,323 B1 | * | 12/2002 | Chow et al. ................. 204/450 |
| 6,514,399 B1 | | 2/2003 | Parce et al. |
| 6,517,234 B1 | | 2/2003 | Kopf-Sill et al. |
| 6,524,456 B1 | | 2/2003 | Ramsey et al. |
| 6,541,768 B1 | | 4/2003 | Andrien, Jr. et al. |
| 6,555,067 B1 | | 4/2003 | Gandhi et al. |
| 6,569,324 B1 | | 5/2003 | Moon et al. |
| 6,576,896 B1 | * | 6/2003 | Figeys et al. ................ 250/288 |
| 6,596,988 B1 | * | 7/2003 | Corso et al. ................. 250/288 |
| 6,602,472 B1 | * | 8/2003 | Zimmermann et al. ..... 422/100 |
| 6,605,472 B1 | | 8/2003 | Skinner et al. |
| 6,607,644 B1 | | 8/2003 | Apffel, Jr. |
| 6,621,076 B1 | * | 9/2003 | van de Goor et al. ...... 250/288 |
| 6,627,076 B1 | | 9/2003 | Griffiths |
| 6,627,882 B1 | | 9/2003 | Schultz et al. |
| 6,632,655 B1 | | 10/2003 | Mehta et al. |
| 6,653,625 B1 | * | 11/2003 | Andersson et al. .......... 250/288 |
| 6,681,788 B1 | | 1/2004 | Parce et al. |
| 6,695,009 B1 | | 2/2004 | Chien et al. |
| 6,709,559 B1 | | 3/2004 | Sundberg et al. |
| 6,733,645 B1 | | 5/2004 | Chow |
| 6,744,046 B1 | | 6/2004 | Valaskovic et al. |
| 6,803,568 B1 | * | 10/2004 | Bousse et al. ............... 250/288 |
| 6,814,859 B1 | * | 11/2004 | Koehler et al. ........... 210/198.2 |
| 6,827,095 B1 | * | 12/2004 | O'Connor et al. ........ 137/15.01 |
| 2001/0037979 A1 | * | 11/2001 | Monn et al. |
| 2002/0036140 A1 | * | 3/2002 | Manz et al. |
| 2002/0041827 A1 | * | 4/2002 | Yager et al. |
| 2002/0100714 A1 | * | 8/2002 | Staats |
| 2002/0110902 A1 | * | 8/2002 | Prosser et al. |
| 2002/0117517 A1 | * | 8/2002 | Unger et al. |
| 2002/0121487 A1 | * | 9/2002 | Robotti et al. |
| 2002/0123153 A1 | * | 9/2002 | Moon et al. |
| 2002/0139931 A1 | * | 10/2002 | Yin et al. |
| 2002/0158195 A1 | * | 10/2002 | Anderson et al. |
| 2002/0170825 A1 | * | 11/2002 | Lee et al. |
| 2002/0182649 A1 | * | 12/2002 | Weinberger et al. |
| 2003/0000835 A1 | | 1/2003 | Witt et al. |
| 2003/0017609 A1 | * | 1/2003 | Yin et al. |
| 2003/0026740 A1 | | 2/2003 | Staats |
| 2003/0029724 A1 | * | 2/2003 | Derand et al. |
| 2003/0047680 A1 | * | 3/2003 | Figeys et al. |
| 2003/0066959 A1 | * | 4/2003 | Andersson et al. |
| 2003/0073260 A1 | * | 4/2003 | Corso |
| 2003/0082080 A1 | * | 5/2003 | Zimmermann et al. |
| 2003/0089605 A1 | * | 5/2003 | Timperman |
| 2003/0089606 A1 | * | 5/2003 | Parce et al. |
| 2003/0106799 A1 | * | 6/2003 | Covington et al. |
| 2003/0111599 A1 | * | 6/2003 | Staats |
| 2003/0146757 A1 | * | 8/2003 | Aguero et al. |
| 2003/0148922 A1 | * | 8/2003 | Knapp et al. |
| 2003/0153007 A1 | * | 8/2003 | Chen et al. |
| 2003/0180965 A1 | * | 9/2003 | Yobas et al. |
| 2003/0213918 A1 | * | 11/2003 | Kameoka et al. |
| 2003/0215855 A1 | * | 11/2003 | Dubrow et al. |
| 2004/0053333 A1 | * | 3/2004 | Hitt et al. |
| 2004/0075050 A1 | * | 4/2004 | Rossier et al. |
| 2004/0096960 A1 | * | 5/2004 | Mehta et al. |
| 2004/0159783 A1 | * | 8/2004 | Gavin et al. |
| 2005/0123688 A1 | * | 6/2005 | Craighead et al. .......... 427/469 |
| 2005/0178960 A1 | * | 8/2005 | Kameoka et al. ........... 250/288 |

FOREIGN PATENT DOCUMENTS

| | | |
|---|---|---|
| WO | WO-9604547 A1 | 2/1996 |
| WO | WO-9636425 A1 | 11/1996 |
| WO | WO 0041214 A1 | 7/2000 |
| WO | WO-0062039 A1 | 10/2000 |
| WO | WO-02/30486 A2 | 4/2002 |
| WO | WO-02030486 A3 | 4/2002 |
| WO | WO-0245865 A1 | 6/2002 |

| | | |
|---|---|---|
| WO | WO-0247913 A1 | 6/2002 |
| WO | WO-02055990 A2 | 7/2002 |
| WO | WO-02080222 A1 | 10/2002 |
| WO | WO-03004160 A1 | 1/2003 |
| WO | WO-03019172 A2 | 3/2003 |
| WO | WO-03054488 A1 | 7/2003 |
| WO | WO-2004044574 A1 | 5/2004 |
| WO | WO-2004051697 A2 | 6/2004 |
| WO | WO-2004062801 A1 | 7/2004 |
| WO | WO-2004067162 A2 | 8/2004 |
| WO | WO-2004070051 A2 | 8/2004 |

OTHER PUBLICATIONS

Chan, Jason H., et al., "Microfabricated Polymer Devices for Automated Sample Delivery of Peptides for Analysis by Electrospray Ionization Tandem Mass Spectrometry", *Anal. Chem., 71,* (1999),4437–4444.

Figeys, Daniel, et al., "Nanoflow Solvent Gradient Delivery from a Microfabricated Device for Protein Identifications by Electrospray Ionization Mass Spectrometry", *Anal. Chem. 70,* (1998),3721–3727.

Jiang, Yun, et al., "Integrated Plastic Microfluidic Devices with ESI–MS for Drug Screening and residue Analysis", *Anal. Chem., 73,* (2001),2048–2053.

Kameoka, Jun, et al., "An Electrospray Ionizatin Source for Integration with Microfluidics", *Anal. Chem, 74,* (2002), 5897–5901.

Koutny, Lance B., et al., "Microchip Electrophoretic Immunoassay for Serum Cortisol", *Anal. Chem., 68,* (1996), 18–22.

Lazar, Iulia M., et al., "Subattomole–Sensitivity Microchip Nanoelectrospray Source with Time–of–Flight Mass Spectrometry Detection", *Anal. Chem., 71,* (1999),3627–3631.

Li, Jianjun, et al., "Separation and Identification of Peptides from Gel–Isolated Membrane Proteins Using a Microfabricated Device for Combined Capillary Electrophoresis/Nanoelectrospray Mass Spectrometry", *Anal. Chem., 72,* (2000),599–609.

Liu, Hanghui, et al., "Development of Multichannel Devices with an Array of Electrospray Tips for High-Throughput Mass Spectrometry", *Anal. Chem., 72,* (2000), 3303–3310.

Ramsey, R. S., et al., "Generating Electrospray from Microchip Devices Using Electroosmotic Pumping", *Anal. Chem., 69,* (1997),1174–1178.

Rocklin, Roy D., et al., "A Microfabricated Fluidic Device for Performing Two–Dimensional Liquid–Phase Separations", *Anal. Chem., 72,* (2000),5244–5249.

Wachs, Timothy, et al., "Electrospray Device for Coupling Microscale Separations and Other Miniaturized Devices with Electrospray Mass Spectrometry", *Anal. Chem., 73,* (2001),632–638.

Xue, Qifeng, et al., "Multichannel Microchip Electrospray Mass Spectrometry", *Anal. Chem., 69,* (1997),426–430.

Zhang, Bailin, et al., "A Microdevice with Integrated Liquid Junction for Facil Peptide and Protein Analysis by Capillary Electrophoresis/Electrospray Mass Spectrometry", *Anal. Chem., 72,* (2000),1015–1022.

"Advanced BioAnalytical Services, Inc. Gains Patent Rights to Novel Microfluidic Handling System", http://www.advion.com/neulicensepress1.html (Archived Apr. 10, 2001), .

"Applied Biosystems, Northeastern University and Professor Barry L. Karger, Ph.D Form Collaboration to Research Advances in Separation Technology for Proteomics", http://www. http://www.advion.com/press/prccorp111901a.html (Archived Jun. 16, 2002) .

"Coming Soon . . . The Advion NanoMate 100", http://www.advion.com/ (archived Apr. 5, 2001), 6 pages.

"Disposable Nano–Electrosprays", http://www.diagnoswiss.com/products/disp nano electr.html(Archived Jun. 5, 2002), 1–2.

"Automated Nanospray", http://www.advion aufiles/AutomatedNanospray/sid001.htm (Archived Jun. 16, 2002), 13 pages.

Auriola, Seppo, et al., "Enhancement of sample loadings for the analysis of oligosaccharides isolated from Pseudomomas aeruginosa using transient isotachophoresis and capillary zone electrophoresis –electrospray –mass spectrometry", *Electrophoresis 1998, 19,* (1998),2665–2676.

Balaguer, E., et al., "Comparsion of Sheathless and Sheath Flow Electrospray Interfaces for On Line Capillary Electrophoresis Mass Spectrometry of Therapeutic Peptide Hormones", 1 page.

Banks, J. F., "Recent advances in capillary electrophoresis/electrospray/mass spectrometry", *Electrophoresis 1997, 18,* (1997),2255–2266.

Banks, Jr., J.F., et al., "Detection of fast Capillary Electrophoresis Peptide and Protein Separations Using electrospray Ionization With a Time–of–Flight Mass Spectrometer", *Anal. Chem., 68,* (1996),1480–1485.

Becker, Holger, et al., "Polymer microfluidic devices", *Talanta 56,* (2002),267–287.

Cao, Ping, et al., "Analysis of Peptides, Proteins, Protein Digests, and whole Human Blood by Capillary Electrophoresis/Electrospray Ionization–Mass Spectrometry Using an In–capillary Electrode Sheathless Interface", *J. Am. Soc. Mass Spectrom 1998, 9,* (1998),1081–1088.

Chang, Yan Z., et al., "Sheathless Capillary Electrophoresis/Electrospray Mass Spectrometry Using a Carbon–Coated Fused–Silica Capillary", *Anal. Chem., 72,* (2000),626–630.

Chen, Shu–Hui, et al., "A Disposable poly(methylmethacrylate)–base microfludic module for protein identification by nanoelectrospray ionization–tandem mass spectrometry", *Electrophoresis 2001, 22,* (2001),3972–3977.

Chen, Yet–Ran, et al., "A Low–Flow CE/Electrospray Ionization MS Interface for Capillary Zone Electrophoresis Large–Vol. Sample Stacking, and Micellar Electrokinetic Chromatograhy", *Anal. Chem., 75,* (2003),503–508.

Chien, Ring–Ling, et al., "Sample Stacking of an Extremely Large Injection vol. in High–Performance Capillary Electrophoresis", *Anal. Chem., 64,* (1992), 1046–1050.

Chiou, Chi–Han, et al., "Micro devices intergrated with microchannels and electrospray nozzles using PDMS casting techiniques", *Sensors and Actuators B, 4311,*(2001), 1–7.

Czaplewski, David A., et al., "Nanofludic Channels with Elliptical Cross Sections", *Applied Physics Letters,* 83(23), (Dec. 8, 2003),4836–4838.

Czaplewski, David A., et al., "Nanomechanical Oscillators Fabricated Using Polymeric Nanofiber Templates", *Nano Letters, 4,* (2004),437–439.

Czaplewski, David A., et al., "Nonlithographic Approach to Nanostructure Fabrication Using a Scanned Electrospinning Source", *Journal of Vacuum Science & Technology B: Microelectronics and Nanometer Structures, 21(6)*, (Nov. 2003),2994–2997.

Deng, Yuzhong, et al., "Chip–Based Quantitative Capillary Electrophoresis/Mass Spectrometry Determination of Drugs in Human Plasma", *Anal. Chem., 73*, (2001),1432–1439.

Ding, Jianmel, et al., "Recent developments in Interfaces and applications", *Analytical Chemistry News & Features: Advances in CE/MS*, (1999), 1–18.

Figeys, Daniel, et al., "A Microfabricated Device for Rapid Protein Identification by Microelectrospray Ion Trap Mass Spectrometry", *Anal. Chem., 69,* (1997),3153–3160.

Figeys, Daniel, et al., "High Sensitivity Analysis of Proteins and Peptides by Capillary Electrophoresis–Tandem Mass Spectrometry: Recent Developments in Technology and Applications", *Electrophoresis, 19,* (1998),885–892.

Figeys, Daniel, et al., "Protein Identification by Solid Phase Microextraction–Capillary Zone Electrophoresis–Microelectrospray–Tandem mass Spectrometry", *Nature Biotechnology, 14,* (1996),1579–1583.

Foret, Frantisek, et al., "Trace Analysis of Proteins by Capillary Zone Electrophoresis With On–Column Transient Isotachophoretic Preconcentration", *Electrophoresis, 14,* (1993),417–428.

Geromanos, Scott, et al., "Injection adaptable Fine Ionization Source ('JaFIS') for Continous Flow Nano–Electrospray", *Rapid Commun. Mass Spectrom., 12,* (1998),551–556.

Geromanos, Scott, et al., "Tuning of an Electrospray Ionization Source for Maximum Peptide–Ion Transmission into a Mass Spectrometer", *Anal. Chem., 72,* (2000),777–790.

Gobry, Veronique, et al., "Microfabricated Polymer Injector for Direct Mass Spectrometry Coupling", *Proteomics 2002, 2,* (2002),405–412.

Guo, Xu, et al., "Analysis of Metallothioneins by Means of Capillary Electrophoresis Coupled to Electrophoresis Coupled to Electrospray Mass Spectrometry with Sheathless Interfacing", *Rapid Commun. Mass Spectrom., 13,* (1999), 500–507.

Hayes, Roger N., et al., "[10] Collision–Induced Dissociation", *Methods in Enzymology, 193,* (1990),237–263.

Issaq, Haleem J., et al., "Seldi–Tof MS for diagnostic Proteomics", *Analytical Chemistry,* (2003),149–155.

Janini, George M., et al., "A Sheathless Nanoflow Electrospray Interface for On–Line Capillary Electrophoresis Mass Spectrometry Mass Spectrometry", *Anal. Chem., 75,* (2003), 1615–1619.

Johnansson, I. M., et al., "Capillary Electrophoresis–Atmospheric Pressure Ionization mass spectrometry for the characterization of peptides", *Journal of Chromatography, 554,* (1991),311–327.

Kaiser, Thorsten, et al., "Capillary Electrophoresis Coupled to Mass Spectrometer for Automated and Robust Polypeptide Determination in Body Fluids for Clinical Use", *Electrophoresis, 25,* (2004),2044–2055.

Kaiser, Thorsten, et al., "Capillary Electrophoresis Coupled to Mass Spectrometry to Establish Polypeptide Patterns in Dialysis Fluids", *Journal of Chromatography A, 1013,* (2003),157–171.

Kameoka, Jun. et al., "A Polymeric Microfluidic Chip for CE/MS Determination of Small Molecules", *Anal. Chem., 73,* (2001),1935–1941.

Kameoka, Jun, et al., "Scanning Tip Electrospinning Source for Deposition of Oriented", *Nanotechnology, 14,* (2003), 1124–1129.

Kameoka, Jun, et al., "An Arrow Shaped Silicon Tip for Polymeric Nanofiber Fabrication", *Journal of Photopolymer Science and Technology, 16,* (2003), 423–426.

Kameoka, Jun, et al., "Fabrication of Oriented Polymeric Nanofibers on Planar Surfaces by Electrospinning", *Applied Physics Letters, 83(2),* (Jul. 14, 2003),371–373.

Kameoka, Jun, et al., "Polymeric Nanowire Architecture", *Journal of Materials Chemistry, 14,* (2004),1503–1505.

Kelly, John F., et al., "Capillary Zone Electrophoresis–Electrospray Mass Spectrometry at Submicroliter Flow Rates: Parctical Considerations and Analytical Performance", *Anal. Chem., 69,* (1997),51–60.

Kim, Jin–Sung, et al., "Microfabricated PDMS Multichannel Emitter for Electrospray Ionization Mass Spectrometry", *J. Am. Soc. Mass Spectrom 2001, 12,* (2001),463–469.

Kim, Jin–Sung, et al., "Microfabrication of Polydimethylsiloxane electrospray ionization emitters", *Journal of Chromatography A, 924,* (2001),137–145.

Kim, Jin–Sung, et al., "Miniaturized multichannel electrospray ionization emitters on poly(dimethylsiloxane) microfluidic devices", *Electrophoresis 2001, 22,* (2001),3993–3999.

Kirby, Daniel P., et al., "A CE/ESI–MS Interface for Stables, Low–Flow Operation", *Anal. Chem., 68,* (1996),4451–4457.

Larsson, Marita, "Transient isotachophoresis for sensitivity enhancement in capillary electrophoresis–mass spectrometry for peptide analysis", *Electrophoreis 2000, 21,* (2000), 2859–2865.

Lee, Edgar D., et al., "On–Line Capillary Zone Electrophoresis–ion spray tandem mass spectrometry for the determination of Dynorphins", *Journal of Chromatography, 458,* (1988),313–321.

Li, JianJun, et al., "Application of Microfludic Devices to Proteomomics Research", *Molecular & Cellular Proteomics 1.2,* (2002),157–168.

Li, Jianjun, et al., "Rapid and Sensitive separation of trace level protein digest using microfabricated devices coupled to a quadrupole –time–of–light mass spectromete"*Electrophoresis 2000, 21,* (2000), 195–210.

Lin, Yuehe, et al., "Microfluidic Devices on Polymer Substrates for Bioanalytical Applications", 10 pages.

Li, Jianjun, et al., "Rapid and Sensitive separation of trace level portein digest using microfabricated devices coupled to a quadrupole –time–of–light mass spectrometer", *Electrophoresis 2000, 21,* (2000),198–210

Liu, Haiqing, et al., "Polymeric Nanowire Chemical Sensor", *Nano Letters, 4,* (2004),671–675.

Moini, Mehdi, "Design and Performance of a Universal Sheathless Capillary Electrophoresis to Mass Spectrometry Interface Using a Split–Flow Technique", *Anal. Chem., 73,* (2001),3497–3501.

Nuehoff, Nils V., et al., "Mass spectrometry for the detection of differentially expressed proteins: a comparsion of surface–enhanced laser desorption/ionization and capillary electrophorsesis/mass spectrometry", *Rapid Communication in Mass Spectrometry, 18,* (2004),149–156.

Neusub, Christian, et al., "A robust approach for the analysis of peptides in the low femtomole range by capillary electrophoresis–tandem mass spectrometry", *Electrophoresis 2002, 23*, (2002),3149–3159.

Oleschuk, Richard D., et al., "Analytical microdevices for mass spectrometry", *trends in analytical chemistry, vol. 19, No. 6*, (2000),379–388.

Olivares, Jose A., et al., "On–Line Mass Spectrometric Detection for Capillary Zone Electrophoresis", *Anal. Chem., 59*, (1987),1230–1232.

Paroni, Rita, et al., "Creatline determination in serum by capillary electrophoresis", *Electrophoresis 2004, 25*, (2004), 463–468.

Premstaller, Andreas, et al., "High–Performance Liquid Chromayography–Electrospray Ionization Mass Spectrometry Using Monolithic Capillary Columns for Proteomic Studies", *Anal. Chem., 73*, (2001),2390–2396.

Rohde, E, et al., "Comparsion of protein mixtures in aqueous humor by membranes preconcentration —capillary electrophoresis —mass spectrometry", *Electrophoresis 1998, 19*, (1998),2361–2370.

Rohner, Tatiana C., et al., "Polymer Microspray with an Intergrated Thick–Film Microelectrode", *Anal. Chem., 73*, (2001),5353–5357.

Sanz–Nebot, Victoria, et al., "Capillary electrophoresis coupled to time of flight–mass spectrometry of therapeutic peptide hormones", *Electrophoresis 2003, 24*, (2003),883–891.

Schmitt–Kopplin, Philippe, et al., "Capillary electrophoresis —mass spectrometry: 15 years of developments and applications", *Electrophoresis 2003, 24*, (2003),3837–3867.

Schultz, Gary A., et al., "A Fully Intergrated Monolithic Microship Electrospray Device for Mass Spectrometry", *Anal. Chem., 72*, (2000),4058–4063.

Selby, D.S., et al., "Direct Quantification of Alkaloid Mixtures by Electrospray Ionization Mass Spectrometry", *Journal of Mass Spectrometry, 33*, (1998),1232–1236.

Smith, Richard D., et al., "Capillary Zone Electrophoresis–Mass Spectrometry Using an Electrospray Ionization Interface", *Anal. Chem., 60*, (1988),436–441.

Smith, Richard D., et al., "New Developments in Biochemical Mass Spectrometry Electrospray Ionization", *Anal. Chem., 62*, (1990),882–899.

Srinivasan, Thara, "ESI and/or CE on Microfluidic Chips: Literature Review", (2002),14 pages.

Stroink, Thom, et al., "On–line coupling of size exclusion and capillary zone electrophoresis via a reversed–phase C18 trapping column for the analysis of Structurally related enkephalins in cerebrospinal fluid", *Electrophoresis 2003, 24*, (2003),897–903.

Svedberg, Malin, et al., "Sheathless from Polymer Microchips", *Anal. Chem., 75*, (2003),3934–3940.

Tang, Ning, "Current Development in SELDI Affinity Technology", *Mass Spectrometry Reviews, 23*, (2004),34–4.

Tang, Keqi, "Generation of Multiple Electrosprays Using Microfabricated Emitter Arrays for Improved Mass Spectrometric Sensitivity", *Anal. Chem., 73*, (2001),1658–1663.

Tempels, F.W. A., et al., "Chromatograhic Preconcentration Coupled To Capillary Electrophoresis via an In–Line Injection Valve", *Anal. Chem., 76*, (2004),4432–4436.

Tomlinson, Andy J., et al., "Investigation of drug metabolism using capillary electrophoresis with photodiode array detection and on–line mass spectrometry equipped with an array detector", *Electrophoresis, 15*, (1994),62–71.

Tomlinson, Andy J., et al., "Systematic development of on–line membrane preconcentration–capillary electrophoresis–mass spectrometry for the analysis of peptide mixtures", *J. Cap. Elec., 002:5*, (1995),225–233.

Tomlinson, Andy J., et al., "Utility of Membrane Preconcentration–Capillary Electrophoresis–Mass Spectrometry in Overcoming Limited Sample Loading for Analysis of Biologically Derived Drug Metabolites, Peptides, and Proteins", *J. Am. Soc. Mass Spectrom, 8*, (1997),15–24.

Valaskovic, Gary A., et al., "Automated Orthogonal Control System for Electrospray Ionization Mass Spectrometry", *New Objective*, 1–5.

Villanueva, Josep, et al., "Serum Peptide Profiling by Magnetic Particle–Assisted, Automated Sample Processing and MALDI–TOF Mass Spectrometry", *Anal. Chem., 76*, (2004),1560–1570.

Von Brocke, Alexander, et al., "Recent advances in capillary electrophoresis/electrospray–mass spectrometry", *Electrophoresis 2001, 22*, (2001),1251–1266.

Wang, Micheal Z., et al., "Analysis of Human serum porteins by liquid phase isoelectric focusing and matrix–assisted laser desorption/ionization–mass spectrometry", *Proteomics 2003, 3*, (2003),1661–1666.

Wen, Jenny, et al., "Microfabricated isoelectric Focusing device for direct electrospray ionization–mass spectrometry", *Electrophoresis 2000, 21*, (2000),191–197.

Whitt, Jacob T., et al., "Capillary Electrophoresis to Mass Spectrometry Interface Using a Porous Junction", *Anal. Chem., 75*, (2003),2188–2191.

Wittke, Stefan, et al., "Determination of peptides and proteins in human urine with capillary electrophoresis–mass spectrometry, a suitable tool for the establishment to new diagnostic markers", *Journal of Chromatography A, 1013*, (2003),173–181.

Wright, Jr., G.L., et al., "Proteinchip surface enhanced laser desorption/ionization (SELD) mass spectrometry: a novel protein biochip technology for detection of prostate cancer biomakers in complex protein mixtures", *Prostate Cancer and Prostatic Diseases, 2*, (1999),264–276.

Yarin, A.L., et al., "Taylor cone and jetting from liquid droplets in electrospinning of nanofibers", *Journal of Applied Physics, 90(9)*, (Nov. 1, 2001),4836–4846.

Zhang, B, et al., "Microfabricated Devices for Capillary Electrophoresis–Electrospray Mass Spectrometry", *Anal. Chem., 71*, (1999),3258–3264.

Zhu, Xiaofeng, et al., "A Colloidal Graphite–Coated Emitter for Shealthless Capillary Electrophoresis/Nanoelectrospray Ionization Mass Spectrometry", *Anal. Chem., 74*, (2002),5405–5409.

* cited by examiner

US 7,105,810 B2

ELECTROSPRAY EMITTER FOR MICROFLUIDIC CHANNEL

RELATED APPLICATIONS

This application claims priority to U.S. Provisional Patent Application Ser. No. 60/342,625, filed Dec. 21, 2001 and Provisional Application No. 60/366,448 filed Mar. 12, 2002, which is incorporated herein by reference.

GOVERNMENT FUNDING

The invention described herein was made with U.S. Government support under agreement number ECS-9876771 awarded by National Science Foundation. The United States Government has certain rights in the invention.

FIELD OF THE INVENTION

The present invention relates to electrospray emitters, and in particular to an electrospray emitter for a microfluidic channel.

BACKGROUND OF THE INVENTION

Chip-based fluid channels are used for many different applications. Applications include zone electrophoresis separation of analytes and capillary electrophoresis performed on chip-based substrates. Various spectroscopic detectors are used do detect the analytes. Attempts to couple mass spectrometry with the chip-based fluid channels involve creating an electrospray of analytes, which is directed to an ion sampling orifice of the mass spectrometer.

Several different attempts to deliver analyte from a microchannel in an electrospray include direct spraying from a flat edge of the chip, the use of a pulled glass capillary, a sleeve to support a sprayer capillary on the edge of the chip, and disposable emitters. Still further prior methods include gluing a pulled capillary sprayer on the flat, larger surface of the chip aligned with the channel. An alternative approach employs a microfabricated monolithic nozzle surrounded by an annular cavity on the surface of a silicon substrate. A still further approach involves an integrated miniaturized pneumatic nebulizer is coupled via a sub-atmospheric liquid junction electrospray interface.

Alternatives to spraying from the chip involve the use of miniaturized ion spray devices that are not formed by microfabrication techniques.

SUMMARY OF THE INVENTION

An electrospray ionization device incorporates a shaped thin film having a tip for coupling with a microfluidic system such as a microfluidic channel. The device may be interfaced to a time-of-flight mass spectrometer (TFOMS).

In one embodiment, the tip is a triangle-shaped thin polymer tip formed by lithography and etching. The microfluidic channel is approximately 20 micrometer wide and 10 micrometers deep, and embossed in a substrate using a silicon master. The channel may be formed in many different types of materials, be many different sizes, and be formed using various processes suitable for the type of material.

The shaped thin film is aligned with the channel and bonded between the channel substrate and a flat plate to create a microfluidic channel with a wicking tip protruding from the end of the channel. An apex of the tip is triangular, curved, trapezoidal, or any other shape that facilitates formation of a Taylor cone. In one embodiment, a stable Taylor cone at the apex of the tip is formed by application of a high potential across the channel, forming an electrospray ionization source. In further embodiments, an integrated array system with multiple channels and integrated tips is formed using the same process used to form a single channel.

DETAILED DESCRIPTION OF THE INVENTION

In the following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

Figure 1:
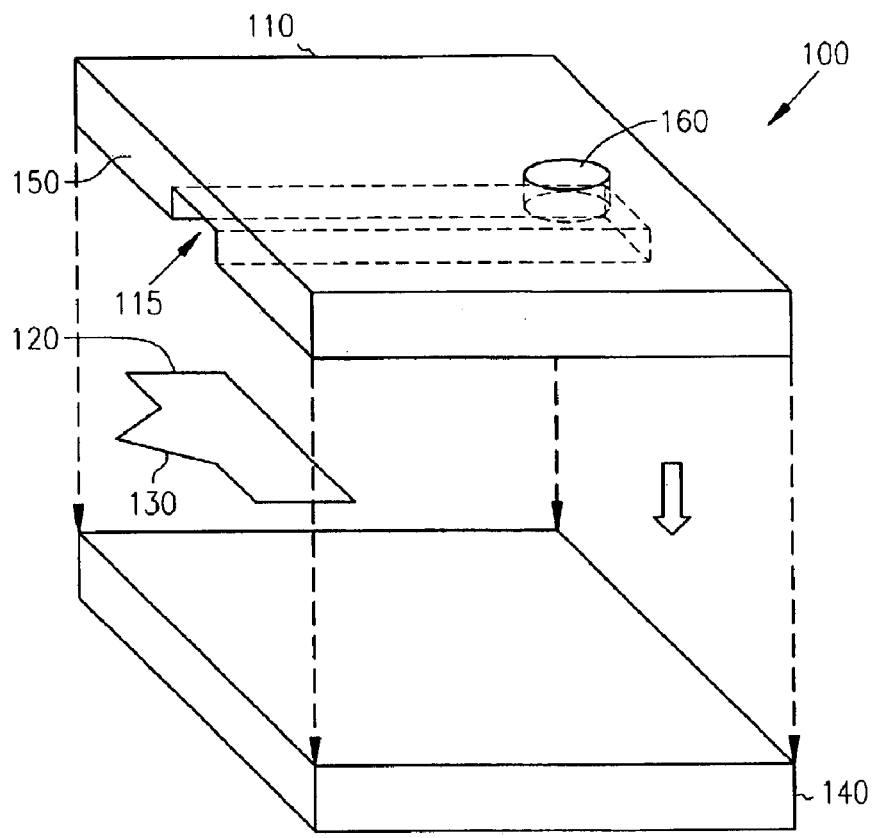
FIG. 1 is an exploded block view example of a channel with integrated electrospray emitter.

An electrospray device is shown at 100 in FIG. 1. In one embodiment, a top chip 110 has a microchannel 115 embossed therein. The device further comprises an emitter film 120, having a triangular or trapezoidal shaped tip 130. The emitter comprises a larger body portion which is rectangular in one embodiment, with the tip 130 extending from the rectangular portion. A bottom chip 140 is thermally bonded with the top chip 110, sandwiching a portion of the emitter film to hold it firmly between the chips. In one embodiment, the film covers a portion of the length of the channel at one end of the bonded chips as indicated at 150. The tip 130 extends laterally from the channel at end 150. A reservoir 160 is coupled to the other end of the channel 115.

In further embodiments, the bottom chip 140 and tip 130 are formed as a single integrated piece, such as by injection molding. The integrated piece is then joined with the top chip 110. In still further embodiments, the electrospray device 100 is formed as a single piece by injection molding or other method to form a thin film tip extending from an edge of a microfluidic system containing structure.

Figure 2:
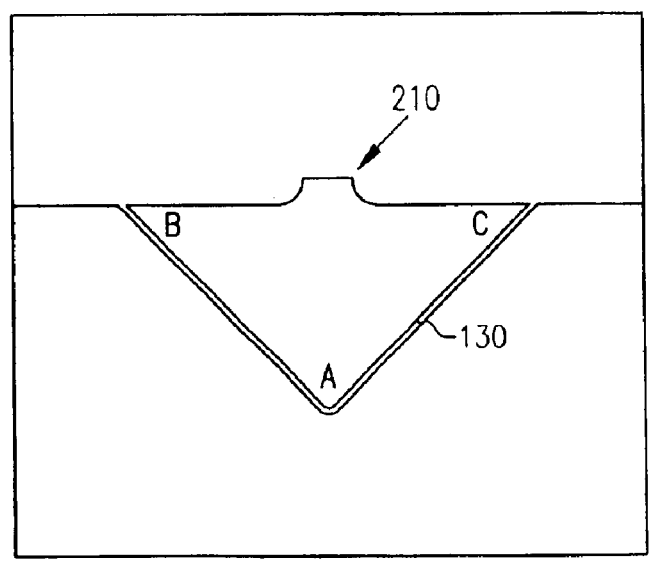
FIG. 2 is a view of a triangular tip electrospray emitter of FIG. 1, taken at a 45 degree angle tilt.

FIG. 2 shows a triangular tip 130 extending from a channel exit 210. The view is taken at a 45 degree tilt angle. The triangle tip acts like a nozzle or wick that helps to form a Taylor cone by guiding the location of a liquid droplet and cone at an apex of the tip. In one embodiment, the tip has an apex with an approximately 90 degree angle, A. Angles B and C, adjacent the channel are approximately 45 degrees. The angle of the apex may be varied, such as between 40 and 120 degrees. At smaller apex angles, liquid may spread at the base of the triangle contacting the microchannel chip, as the wetting angle of solutions in the channel may be smaller than the angles the base of the triangle makes with the chip.

Different apex angles may be optimal for solutions with different wetting angles. In one embodiment, the base of the triangular tip is approximately 100 micrometers, and the height is approximately 50 micrometers. Thus, the base extends well beyond both sides of the channel when centered approximately at the center of the channel. As seen in FIG. 2, the apex has a small radius of curvature. The apex may be sharp if desired, and in further embodiment, the radius of curvature may be varied significantly. Many different shapes that promote formation of a Taylor cone may be used.

Figure 3:
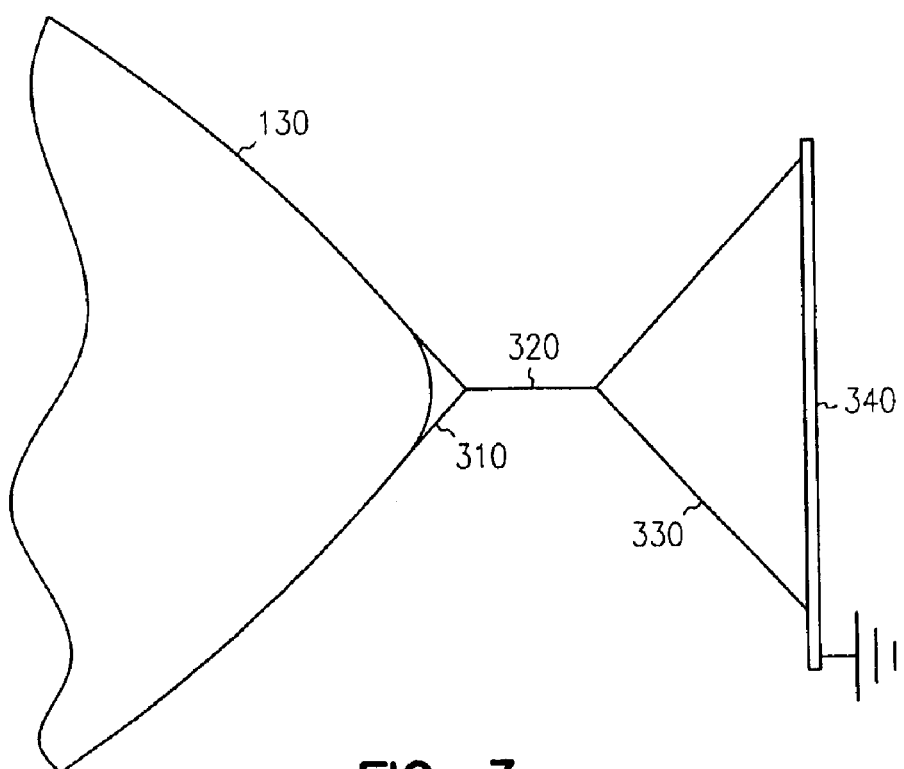
FIG. 3 is an example representation of Taylor cone formation from a triangle tip electrospray emitter.

The shape of the tip 130 helps form and fix a position of a Taylor cone 310, as shown in FIG. 3. When a difference in potential is applied to the device, a liquid droplet with a critical curvature for establishing a Taylor cone is formed at the apex of the tip. A liquid jet 320 is formed at the apex. Highly charged small liquid droplets are made at a liquid plume 330 extending toward a counter electrode 340. Excess electrostatic force extracts liquid from the apex of the Taylor cone to establish the liquid jet. The liquid jet 320 is branched at the plume 340 region due to repelling force acting among positively charged small droplets.

Figure 4:
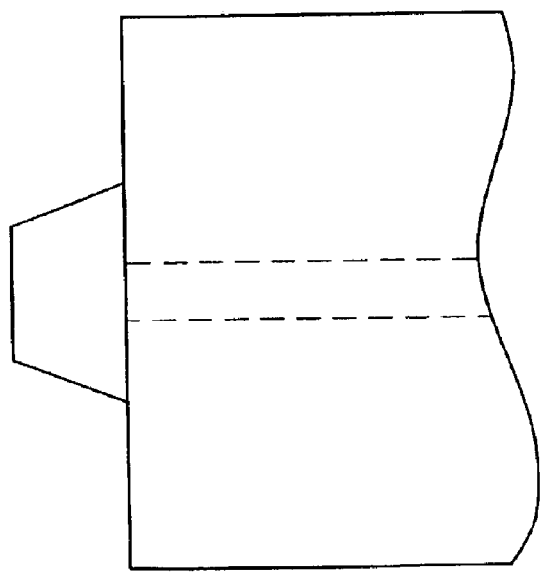
FIG. 4 is a representation of a trapezoidal shaped emitter film.

FIG. 4 is a representation of a trapezoidal shaped emitter film. In one embodiment, the trapezoidal shaped emitter film comprises a body portion bonded between the chips, and a trapezoidal portion extends laterally from the channel. A long edge of the trapezoidal portion adjacent the channel is approximately 140 micrometers, and extends approximately 100 micrometers from the edge to an apex comprising a shorter edge of the trapezoidal portion at which the Taylor cone is formed.

Formation of the emitter uses standard photolithographic processing of a four inch silicon wafer. First, a 5 micrometer layer of parylene, such as parlyene C is formed on the wafer by one of many methods, such as by deposition. Photoresist is formed on top of the parylene layer and patterned in a shape of the desired emitter shape. The wafer is then etched in plasma therm PT 72 using oxygen plasma for 15 micrometer depth; 5 micrometers from parylene and 10 micrometers from photoresist. The photoresist is removed by acetone or other means, and the remaining parylene is peeled off to form one or more thin film emitters. In one embodiment, the film is peeled off in an isopropyl alcohol solution. Such films may exhibit hydrophilic properties.

Figure 5:
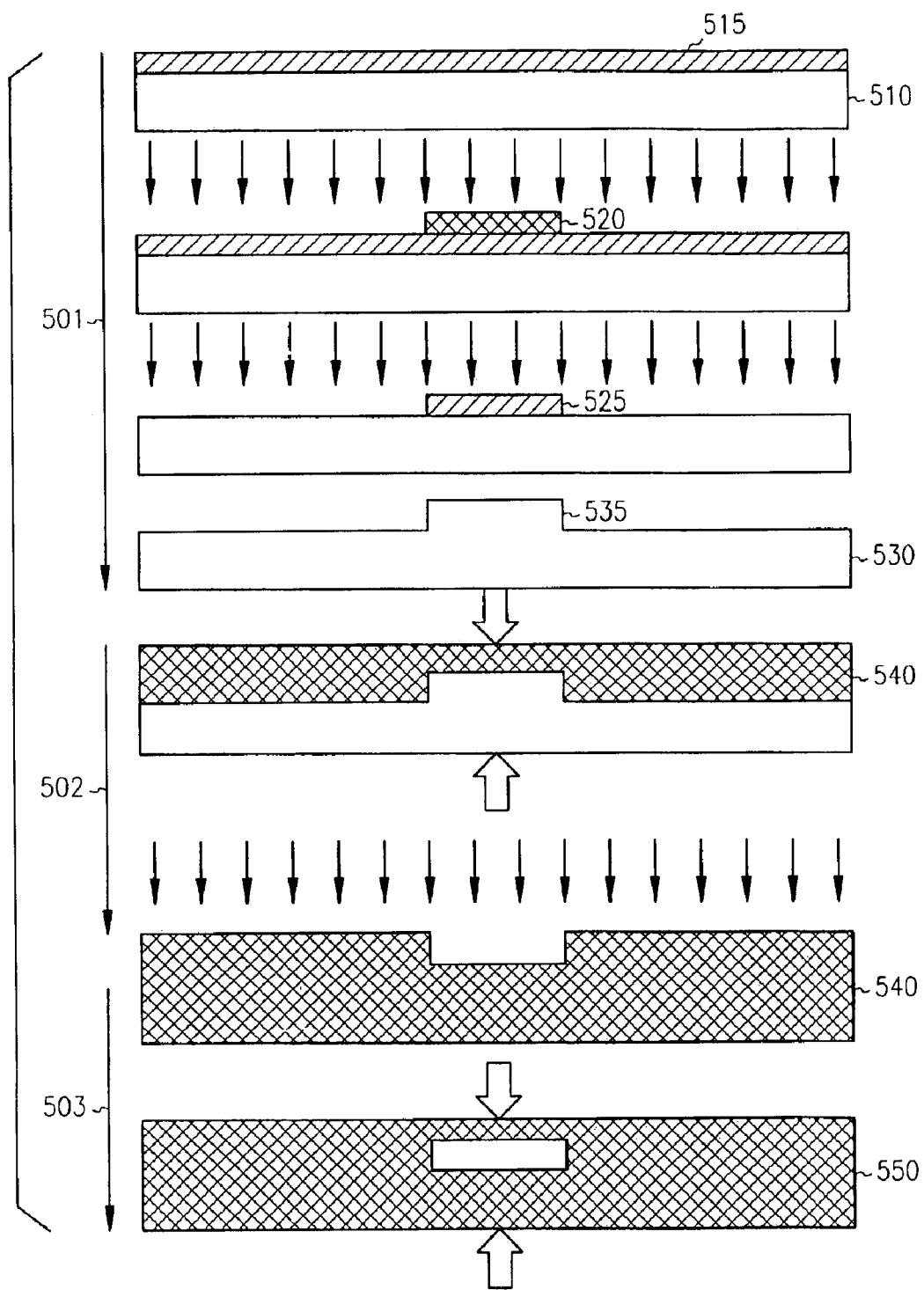
FIG. 5 is a series of cross section examples showing formation of the channel with integrated electrospray emitter of FIG. 1.

FIG. 5 shows several cross sections representing a fabrication process for the device 100. A silicon master is formed at 501, followed by embossing 502 to form a polymer base, which is bonded at 503, sandwiching the emitter. In one embodiment, the polymer base comprises a cyclo olefin polymer plastic plate. A silicon wafer 510 has a photoresist formed on one side such as by spinning, or any other suitable method. A mask 520 is used block exposure of a portion of the photoresist to UV light, resulting in a patterned layer of photoresist 525. An $SF_6$ plasma etch is then performed to create a silicon master 530 having an embossing pattern 535 corresponding to a desired channel. In one embodiment, a 2.5 centimeters, 20 micrometer wide, and 10 micrometer deep microfluidic channel is embossed in a polymer chip 540 using the silicon master. A reservoir hole is also formed in the polymer chip if desired, such as by drilling. The embossed polymer chip 540 is subjected to an $O_2$ plasma.

In various embodiments, the channel width varies from about 20 um to about 60 um and the range of the channel depth is from about 10 um to about 20 um. The thickness of the emitter film is 3 um to 10 um. The apex angle of the emitter film is smaller than 90 degrees. The width of microfluidic channel is smaller than that of the bottom of the triangular tip or is approximately the same size as the boom of the triangular tip. Instead of polymeric materials, metal material or ceramics can be used for the tip. The above parameters are approximate, and may be varied significantly in further embodiments.

The emitter is sandwiched between the embossed polymer chip 540 and a cover chip 550, also formed of polymer in one embodiment. The emitter is aligned such that an edge of the rectangular portion lines up with the side of the chip at the channel exit side of the chip. The tip 130 extends from the edge of the rectangular portion and side of the chip from the channel. In one embodiment, the triangular portion is centered on a center axis of the channel. Pressure and heat are applied to bond the chips, with the emitter positioned at the end of the channel to serve as an electrospray tip. In one embodiment, the chips and emitter were subjected to pressure and heated to 85 degrees C. for 10 to 15 minutes using a mini test press machine.

Figure 6:
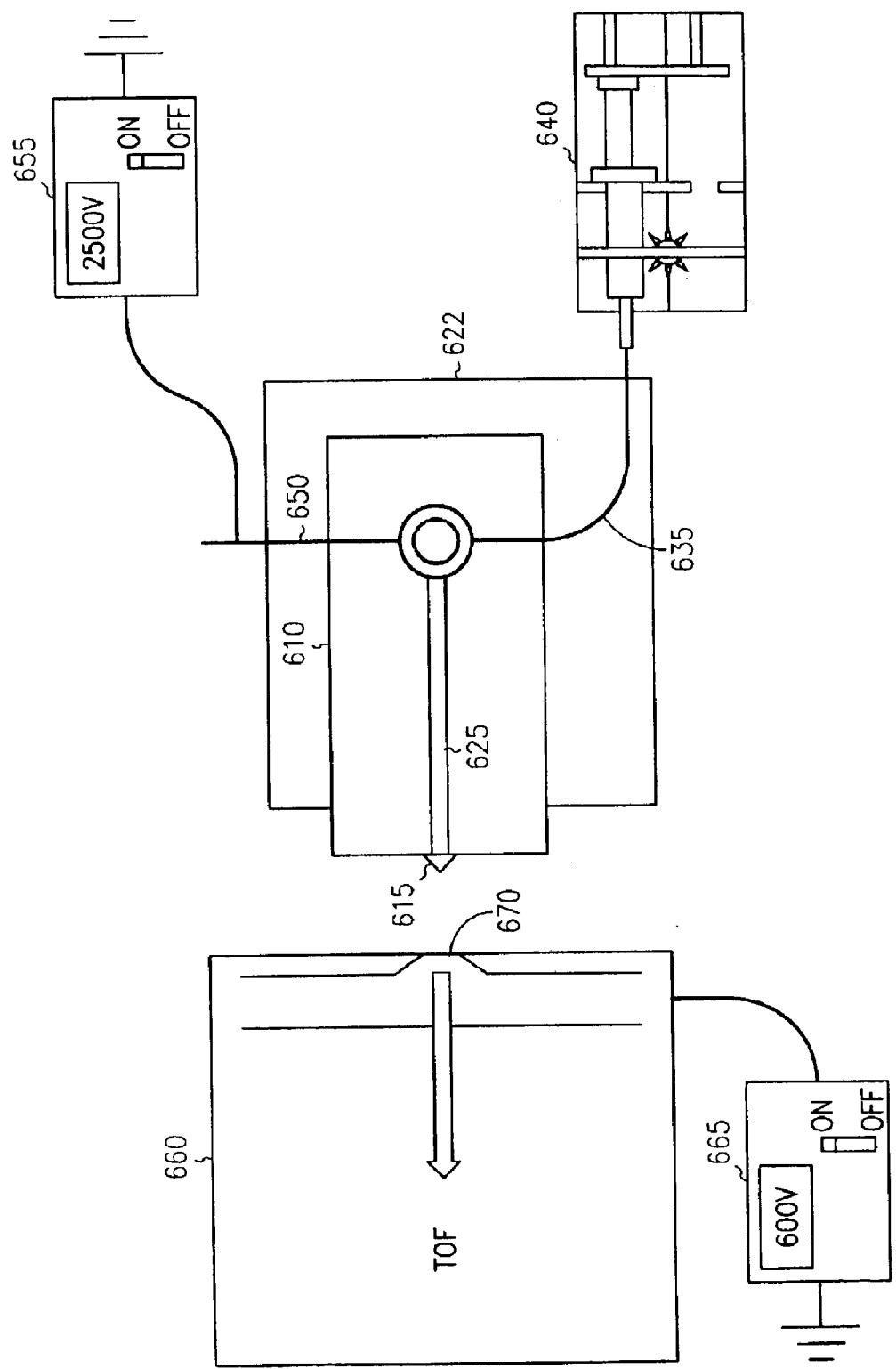
FIG. 6 is a block circuit diagram of an electrospray device coupled to a mass spectrometer.

FIG. 6 illustrates integration of an electrospray device 610 having a triangle emitter 615 with a time of flight (TOF) mass spectrometer 620. In one embodiment, the device 610 is mounted on an X, Y, Z stage 622 for adjustment to provide maximum ion current. The triangle emitter 615 is positioned at one end, an exit of a channel 625. Another end of the channel 625 is coupled to a reservoir 630. The reservoir has a capillary tube 635, or other fluid transport mechanism that couples it to a pump 640 to provide fluid to the reservoir and hence to the channel. In one embodiment, the capillary tube is formed of silica and coupled to the channel via a pipet tip glued to the reservoir 630. In further embodiments, reservoir 630 is representative of further reservoirs that are provided along the channel 625 to facilitate desired separation of molecules. Examples of such reservoirs include buffer reservoirs, waste reservoirs and sample reservoirs. Selected reservoirs may be coupled via a T junctions with the channel 625.

The reservoir 630, in one embodiment also has a conductive wire 650, such as a gold wire coupling it to a power supply 655 for electrospray ionization. Glue is one method used to couple the wire to the reservoir. In one embodiment, power supply 655 provides 2500 volts to the reservoir. An aluminum counter electrode 660 is positioned approximately 10 millimeters from the tip of triangle emitter 615, and is also coupled to a power supply 665 providing approximately 600 volts. The X,Y,Z stage provides the ability to adjust the distance between the emitter 615 and an orifice 670 of the mass spectrometer 620. Thus, the voltages need not be the same as those used in this example, as the distance may be adjusted to optimize total ionic current. In further embodiments, the device 610 is fixed with respect to the mass spectrometer, or the mass spectrometer is moved.

In one example, the mass spectrometer is maintained at a temperature of approximately 80 degrees C. via internal or external heaters. The pump is a syringe pump, and provides a stable flow of approximately 300 nanoliters per minute to supply liquid to the channel outlet proximate emitter 615. A voltage of between approximately 2500 to 3000 volts is applied between the wire 650 and the orifice 670 with the orifice between 8 to 12 millimeters from the tip of the emitter 615 to produce a suitable spray. The voltage required to produce an optimal Taylor cone varies at least with tip shape, fluid flow rates, and distances to the electrode.

Figure 7:
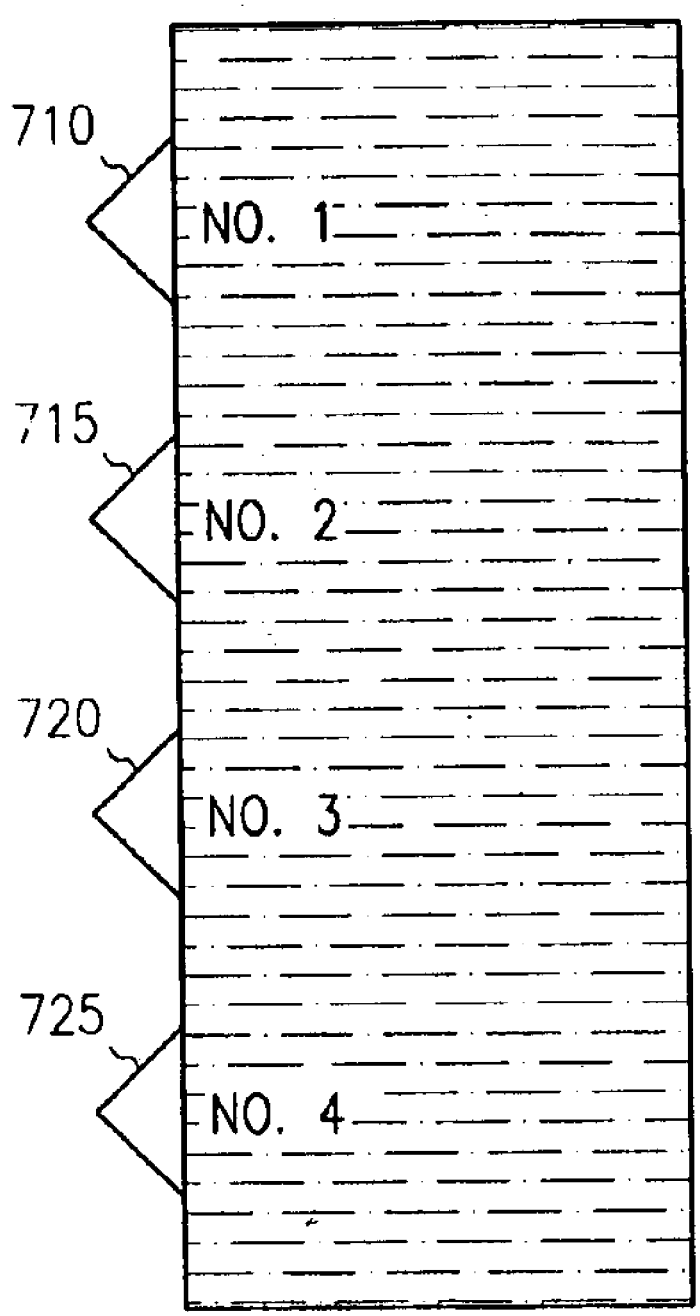
FIG. 7 is a block representation of a multi-tip electrospray emitter device.

FIG. 7 is a block representation of a multi-tip electrospray emitter device. Four triangle emitters 710, 715, 720 and 725 are shown. Each emitter is coupled to a channel. The may be operated in parallel, or may be sequentially operated. When operated in parallel, the emitters are spaced sufficiently to minimize interference between the respective sprays. A multichannel system when operated in a multiplexed manner operates reliably with no significant cross contamination between the channels.

CONCLUSION

A thin film tip is integrated with a microchannel to form an electrospray of fluid from the microchannel. Dimensions of the thin film tip and microchannel may be varied significantly from the described embodiments. Shapes of thin film tips may also be varied in different polygonal configurations as desired to provide the ability to form a Taylor cone when subjected to a large difference in potential. The potential may also be varied. Materials selected for formation of the tip and channel may also be varied. The materials described provide for ease of manufacture using microfabrication techniques. Such materials are also compatible with various fluids used in separation processes. Other materials may also be utilized with similar or different manufacturing processes. Many different plastics may be used, as well as silicon or other materials. Embossing may be used with various plastics, and semiconductor processing may be utilized with silicon based substrates.

The microchannel and tip combination may be integrated with other microfluidic structures, and is also useful in conjunction with a time of flight mass spectrometer. In one embodiment, the combination is positioned such that an electrospray is provided to an orifice of the spectrometer to provide the spectrometer a suitable spray for spectroscopic analysis.

What is claimed is:

1. An electrospray device comprising:
a chip having a microchannel extending to an edge of the chip;
a cover; and
an emitter film having a polygonal tip sandwiched between the chip and the cover such that the polygonal tip extends from such edge of the chip.

2. The electrospray device of claim 1 and further comprising a reservoir formed in the chip and coupled to the microchannel.

3. The electrospray device of claim 1 wherein the tip of the emitter film is triangular in shape.

4. The electrospray device of claim 3 wherein the tip of the emitter film has an apex angle of between 40 and 140 degrees.

5. The electrospray device of claim 3 wherein the tip of the emitter film has an apex angle of approximately 90 degrees.

6. The electrospray device of claim 1 wherein the emitter film comprises a body portion, and a triangular tip extending from the body portion.

7. The electrospray device of claim 6 wherein the body portion is sandwiched between the chip and the cover, and has an edge substantially aligned with edges of the chip and the cover.

8. The electrospray device of claim 7 wherein the tip is located on the edge of the body that is aligned with the edges of the chip and cover, and the tip is approximately coaxial with the channel and extends from the edges.

9. The electrospray device emitter of claim 1 wherein the polygonal electrospray emitter is formed of material compatible with microfabrication techniques.

10. The electrospray device of claim 9 wherein the chip is formed of cyclo olefin polymer.

11. The device of claim 1 wherein the chip and electrospray emitter films are a single integrated piece.

12. The electrospray device of claim 11 wherein the apex is curved.

13. The electrospray device of claim 12 wherein the apex has a desired radius of curvature.

14. The electrospray device of claim 1, wherein the emitter film is formed with a triangular shape and the polygonal tip of the emitter film is curved.

15. An electrospray device comprising:
a chip having a microchannel with a first end extending to an edge of the chip;
a reservoir coupled to the microchannel;
a cover;
an emitter film haging a polygonal tip sandwiched betweenthe chip and the cover such that the polygonal tip extends from such edge of the chip; and
a power supply coupled to the reservoir.

16. The electrospray device of claim 15 and further comprising a counter electrode positioned a desired distance rom the polygonal tip.

17. The electrospray device of claim 15 wherein the polygonal electrospray emitter comprises a triangular shape or trapezoidal shape.

18. The electrospray device of claim 15 wherein the emitter film is formed of material compatibl with microfabrication techniques.

19. The nanospray emitter of claim 18 wherein the chip comprises cyclo olefin polymer.

20. An electrospray device comprising:
a chi having a microchannel with a first end extending to an edge of the chip;
a reservoir coupled to the microchannel;
a cover;
an emitter film having a polygonal tip sandwiched between the chip and the cover such that the polygonal tip extends from such edge of the chip;
a power suply coupled to the reservoir; and
a counter electrode positioned a desired distance from the polygonal tip wherein a voltage across the power supply and counter electrode causes a Taylor cone of fluid from the channel to form on the tip.

21. The electrospray device of claim 20 and further comprising a mass spectrometer having an orifice positioned opposite the Taylor cone and spaced from the tip sufficiently to receive an electrospray from the Taylor cone.

22. A method of makiong an electrospray device, the method comprising:
forming a microchannel on a substrate running to an edge of the substrate;
obtaining a thin filmemitter having a body portion with a polygonal tip on an edge of the body portion;
bonding the substrated and a cover with at least part of the body portion of thin film emitter between the substrate and cover such that the tip extends from the channel at the end of the edge of the substrate.

23. The method of claim 22 wherein the thin film emitter is formed of material compatible with microfabrication techniques.

24. The method of claim 23 wherein the substrate is formed of a cyclo olefin polymer plastic plate.

25. The method of claim 22 and further comprising creating an embossing master that is used to form the microchannel.

26. The method of claim 25, wherein the embossing master is formed from a silicon based substrate.

27. The method of claim 22 wherein the thin film emitter is obtained by patterning a polymer or silicon layer on the substrate in the shape of the desired emitter.

28. The method of claim 27 wherein the polymer or silicon layer is patterned by lithography followed by a plasma etch.

29. The method of claim 26 wherein the patterned polymer or silicon layer is peeled off the substrate in an isopropyl alcohol solution.

30. An electrospray device comprising:
a chip having a covered microfluidic structure that delivers fluid to an edge of the chip; and
a planar emitter having a tip coupled to the edge of the chip and extending therefrom, wherein the tip has anapex shaped to facilitate formation of a Taylor cone from fluid delivered to the edge of the chip.

31. The electrospray device of claim 30 wherein the tip is triangular shaped.

32. The electrospray device of claim 30 wherein the apex is curved.

33. The electrospray device of claim 30 wherein the microfluidic structure comprises a channel, and where a width of the emitter is wider than a width of the channel.

34. The electrospray device of claim 33 wherein the emitter is approximately coaxial with the channel.

35. A microfluidic chip comprising:
a top chip portion that is formed with at least one microchannel extending to an edge of the top chip portion;
a bottom chip portion coupled to the top chip portion; and
an electrospray emitter found as a single integrated piece with the bottom chip portion, wherein the electrospray emitter extends from the ege of the top chip portion for directing an electrospray from the microfluidic chip.

36. The microfluidic chip of claim 30, wherein the electrospray emitter is formed with a triangular shape.

37. The microfluidic chip of claim 36, wherein the electrospray emitter has a tip with an apex angle of between 40 and 140 degrees.

38. The microfluidic chip of claim 37, wherein the electrospray emitter tip has a trapezoidal configuration.

39. The microfluidic chip of claim 35, wherein the electrospray emitter is approximately coaxial with the microchannel formed in the top chip portion.

40. The microfluidic chip of claim 35, wherein the electrospray emitter is formed with a triangular shape and has a curved tip.

41. The microfluidic chip of claim 40, wherein the curved tip has a small radius of curvature.

42. The microfluidic chip of claim 40 wherein the electrospray emitter has a base which extends beyond both sides of the microchannel and is approximately coaxial with the microchannel.

43. An electrospray ionization device and mass spectrometer interface comprising:
a covered microfluidic structure formed with a reservoir in fluid communication with a microchannel that delivers fluid to an exit side of the microfluidic structure; and
an electrospray emitter extending from the edge of the microfluidic structure that is formed as a single integrated piece with at least a portion of the microfluidic structure;
a mass spectrometer having an orifice for receiving and electrospray from the emitter; and
a power supply system connected to the reservoir and a counter electrode positioned substantially adjacent to the emitter for applying a voltage to emit at least a portion of the electrospray from the emitter into the orifice of the mass spectrometer.

44. The electrospray ionization device and mass spectrometer interface as recited in claim 39, further comprising an XYZ stage that movably supports the electrospray ionization device relative to the orifice of the mass spectrometer.

45. The electrospray ionization device and mass spectrometer interface as recited in claim 43, wherein the covered microfluidic structure is formed as a single piece.

46. The electrospray ionization device and mass spectrometer interface as recited in claim 43, wherein the emitter is formed with a thin-film tip.

47. An electrospray device comprising:
a covered microfluidic structure formed with a micrchannel that delivers fluid to a selected surface of the microfluidic structure; and
a wicking tip extending from the selected surface of the microfluidic structure that is formed as a single integrated place with at least a portion of the microfluidic structure, wherein the tip is configured with a predefined shape to facilitate formation of a Taylo cone when fluid is sprayed therefrom.

48. The electrospray device of claim 47 wherein the microfluidic structure includes a top portion that forms the single integrated piece with the wicking tip.

49. The electrospray device of claim 47, wherein the microfluidic structure includes a bottom portion that forms the single integrated piece with the wicking tip.

50. A device comprising:
a chip having a microchannel extending to an edge of the chip;
a cover; and
an electrospray emitter film having an apex, wherein the electrospray emitter film is sandwiched between the chip and the cover such that the apex extends from the edge of the chip.

51. The electrospray device of claim 50, wherein the apex is curved.

52. The electrospray device of claim 51 wherein the apex has a desired radius of curvature.

53. The microfluidic chip of claim 50, wherein the electrospray emitter apex has an apex angle of between 40 and 140 degrees.

54. A device comprising:
a chip having a microchannel extending to an edge of the chip; a cover; and
emitter means extending from the edge of the chip and coupled to the microchannel for emitting an electrospray from fluid flowing through the microchannel.

55. The device of claim 54, wherein the means for emitting an electrospray creates a Taylor cone.

56. The device of claim 55 wherein the means for emitting an electrospray wicks fluid from the microchannel.

57. A device comprising:
a chip having multiple microchannels extending to an edge of the chip;
a cover; and
a plurality of electrospray emitter films, each having an apex, wherein the electrospray emitter films are disposed between the chip and the cover such that each apex extends from a microchannel at the edge of the chip.

58. The microfluidic chip of claim 57, wherein the electrospray emitter apex has an apex angle of between 40 and 140 degrees. emitter apex has an apex angle of between 40 and 140 degrees.

* * * * *

UNITED STATES PATENT AND TRADEMARK OFFICE
CERTIFICATE OF CORRECTION

PATENT NO. : 7,105,810 B2
APPLICATION NO. : 10/394757
DATED : September 12, 2006
INVENTOR(S) : Kameoka et al.

It is certified that error appears in the above-identified patent and that said Letters Patent is hereby corrected as shown below:

On the Title page, in field (60), under "Related U.S. Application Data", in column 1, line 3, delete "12," and insert -- 21, --, therefor.

On the Title page, in field (56), under "U.S. Patent Documents", in column 1, line 1, after "4,443,319 A" delete "*".

On the Title page, in field (56), under "U.S. Patent Documents", in column 1, line 2, after "4,483,885 A" delete "*".

On the Title page, in field (56), under "U.S. Patent Documents", in column 1, line 3, after "4,963,736 A" delete "*".

On the Title page, in field (56), under "U.S. Patent Documents", in column 1, line 4, after "5,296,114 A" delete "*".

On the Title page, in field (56), under "U.S. Patent Documents", in column 2, line 1, after "5,358,618 A" delete "*".

On the Title page, in field (56), under "U.S. Patent Documents", in column 2, line 2, after "5,395,975 A" delete "*".

On the Title page, in field (56), under "Other Publications", in column 2, line 3, after "3296" insert -- . --.

In column 5, line 33, in Claim 1, after "comprising" delete ";" and insert -- : --, therefor.

In column 6, line 6, in Claim 14, after "and" insert -- wherein --.

In column 6, line 13, in Claim 15, delete "haging" and insert -- having --, therefor.

In column 6, line 14, in Claim 15, delete "betweenthe" and insert -- between the --, therefor.

In column 6, line 19, in Claim 16, delete "rom" and insert -- from --, therefor.

In column 6, line 24, in Claim 18, delete "compatibl" and insert -- compatible --, therefor.

In column 6, line 29, in Claim 20, delete "chi" and insert -- chip --, therefor.

UNITED STATES PATENT AND TRADEMARK OFFICE
CERTIFICATE OF CORRECTION

PATENT NO. : 7,105,810 B2
APPLICATION NO. : 10/394757
DATED : September 12, 2006
INVENTOR(S) : Kameoka et al.

It is certified that error appears in the above-identified patent and that said Letters Patent is hereby corrected as shown below:

In column 6, line 36, in Claim 20, delete "suply" and insert -- supply --, therefor.

In column 6, line 45, in Claim 22, delete "makiong" and insert -- making --, therefor.

In column 6, line 49, in Claim 22, delete "filmemitter" and insert -- film emitter --, therefor.

In column 6, line 51, in Claim 22, delete "substrated" and insert -- substrate --, therefor.

In column 6, line 52, in Claim 22, delete "portion of" insert -- the --.

In column 6, line 66, in Claim 27, delete "the" and insert -- a --, therefor.

In column 7, line 2, in Claim 28, delete "patterened" and insert -- patterned --, therefor.

In column 7, line 4, in Claim 29, delete "claim 26" and insert -- claim 28 --, therefor.

In column 7, line 13, in Claim 30, delete "anapex" and insert -- an apex --, therefor.

In column 7, line 29, in Claim 35, delete "found" and insert -- formed --, therefor.

In column 7, line 31, in Claim 35, delete "ege" and insert -- edge --, therefor.

In column 7, line 33, in Claim 36, delete "claim 30," and insert -- claim 35, --, therefor.

In column 7, line 61, in Claim 43, delete "and" and insert -- an --, therefor.

In column 8, line 2, in Claim 44, delete "claim 39," and insert -- claim 43, --, therefor.

In column 8, lines 13–14, in Claim 47, delete "micrchannel" and insert -- microchannel --, therefor.

In column 8, line 18, in Claim 47, delete "place" and insert -- piece --, therefor.

In column 8, line 20, in Claim 47, delete "Taylo" and insert -- Taylor --, therefor.

In column 8, line 22, in Claim 48, after "claim 47" insert -- , --.

UNITED STATES PATENT AND TRADEMARK OFFICE
CERTIFICATE OF CORRECTION

PATENT NO. : 7,105,810 B2
APPLICATION NO. : 10/394757
DATED : September 12, 2006
INVENTOR(S) : Kameoka et al.

It is certified that error appears in the above-identified patent and that said Letters Patent is hereby corrected as shown below:

In column 8, line 36, in Claim 51, after "claim 50" delete ",".

In column 8, lines 64–65, in Claim 58, after "140 degrees." delete "emitter apex has an apex angle of between 40 and 140 degrees.".

Signed and Sealed this

Twenty-seventh Day of February, 2007

JON W. DUDAS
*Director of the United States Patent and Trademark Office*